(12) United States Patent
Murata et al.

(10) Patent No.: US 9,364,438 B2
(45) Date of Patent: Jun. 14, 2016

(54) PROCESS FOR PRODUCING SOLID PARTICLES

(71) Applicant: Takeda Pharmaceutical Company Limited, Osaka (JP)

(72) Inventors: Naoyuki Murata, Osaka (JP); Shigeo Yanai, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/430,956

(22) PCT Filed: Sep. 25, 2013

(86) PCT No.: PCT/JP2013/075948
§ 371 (c)(1),
(2) Date: Mar. 25, 2015

(87) PCT Pub. No.: WO2014/050910
PCT Pub. Date: Apr. 3, 2014

(65) Prior Publication Data
US 2015/0250728 A1    Sep. 10, 2015

(30) Foreign Application Priority Data
Sep. 26, 2012    (JP) ................................. 2012-212264

(51) Int. Cl.
*A61K 9/14* (2006.01)
*A61K 31/18* (2006.01)
*A61K 31/24* (2006.01)
*A61K 9/16* (2006.01)

(52) U.S. Cl.
CPC .................. *A61K 9/1688* (2013.01); *A61K 9/14* (2013.01); *A61K 31/18* (2013.01); *A61K 31/24* (2013.01)

(58) Field of Classification Search
None
See application file for complete search history.

(56) References Cited

U.S. PATENT DOCUMENTS

2009/0297565 A1    12/2009    Müller et al.

FOREIGN PATENT DOCUMENTS

| | | |
|---|---|---|
| JP | 2011-194366 | 10/2011 |
| WO | 03/045353 | 6/2003 |

OTHER PUBLICATIONS

English translation of Written Opinion issued Oct. 22, 2013 in PCT/JP2013/075948.
International Search Report issued Oct. 22, 2013 in International (PCT) Application No. PCT/JP2013/075948.
E. Merisko-Liversidge et al., "Nanosizing: A Formulation Approach for Poorly-Water-Soluble Compounds", European Journal of Pharmaceutical Sciences, vol. 18, pp. 113-120, 2003.
Extended European Search Report issued Apr. 20, 2016 in corresponding European Application No. 13840884.4.
Mitali Kakran et al., "Fabrication of quercetin nanocrystals: Comparison of different methods", European Journal of Pharmaceutics and Biopharmaceutics, 80, 2012, pp. 113-121.

*Primary Examiner* — Yevegeny Valenrod
(74) *Attorney, Agent, or Firm* — Wenderoth, Lind & Ponack, L.L.P.

(57) ABSTRACT

A method of producing crystal of a poorly water-soluble pharmaceutical compound, including mixing a solution of a poorly water-soluble pharmaceutical compound in a good solvent and nanobubble water or an aqueous nanobubble solution to precipitate crystal of the poorly water-soluble pharmaceutical compound. The crystal of a poorly water-soluble pharmaceutical compound obtained by the method is microparticulate and has more uniform particle size distribution, and is superior in the absorbability and sustainability.

4 Claims, 2 Drawing Sheets

PROCESS FOR PRODUCING SOLID PARTICLES

TECHNICAL FIELD

The present invention relates to a production method of solid particles of a poorly water-soluble pharmaceutical compound by using a crystallization method and solid particles of the pharmaceutical compound obtained thereby. More particularly, the present invention relates to a production method of solid particles of a poorly water-soluble pharmaceutical compound, comprising, in a poor solvent precipitation method, using nanobubble water or an aqueous nanobubble solution as a poor solvent, and solid particles of a poorly water-soluble pharmaceutical compound having improved dispersibility or absorbability, which are obtained by the method.

BACKGROUND OF THE INVENTION

Crystallization method is a method of precipitating crystals by utilizing crystallization phenomenon in a non-equilibrium state, where supersaturation is a driving power. For crystallization of a pharmaceutical compound, an Anti-solvent (poor solvent) Crystallization method capable of operating at ambient temperature is often used to avoid heat denaturation of the object compound. The poor solvent crystallization method is a method including dissolving a compound, which is insoluble in water and the like, in a good solvent, and mixing the compound solution with another solvent (water etc.) to allow for precipitation of crystals by creating a supersaturation state of the solution. The crystals obtained by this method have high purity, and the yield of the solute is determined by the kind and the amount added of the poor solvent. Therefore, crystals can be obtained at a high yield rate from a solution having a high solubility, and the method is drawing attention as a means for improving the yield of a pharmaceutical compound. At present, there are many products using the crystallization method (non-patent document 1). It is also possible to use the crystallization method for amorphous forms, which confers crystallinity by heating/cooling or pressurizing/reducing pressure and the like.

However, since the technique for highly controlling the crystal quality is immature, microparticulation, achievement of uniform particle size distribution and the like are the problems. When the pharmaceutical compound is poorly water-soluble and has a large particle size, the dispersibility during formulation of a liquid medicine becomes poor, and addition of an additive to the solvent is required. When an injection is prepared, a large-sized injection needle is required, which problematically increases the burden on patients. Therefore, respective researchers use a high-pressure crystallization apparatus (PureNano etc.), a high-pressure homogenizer, a homogenizer, Starburst and the like, Wet-Milling apparatus and the like for microparticulation and improvement of particle size distribution (non-patent document 2). They are defective in that the former (high-pressure crystallization apparatus, high-pressure homogenizer, homogenizer, Starburst etc.) requires high energy, and the latter (Wet-Milling apparatus) generally requires a long operation time, shows a decreased yield, has difficulty in large-scale operation and the like. The development of a crystallization method capable of preparing fine crystals having a uniform particle size and permitting easy microparticulation and homogenization operation after precipitation has been desired.

Patent document 1 describes a method of producing nano-sized particles and hollow particles by, in poor solvent crystallization, generating air bubbles in a poor solvent, mixing the solvent with an organic pigment solution, and precipitating fine particles of the organic pigment on the surface of the air bubbles. As a means for generating the air bubbles, a swirling flow-type micro-bubble generator and an ultrasonication generator that generates micro cavities are described. However, since the particle size tends to grow as the degree of crystallinity of the organic pigment increases, a microparticulation method including crushing air bubbles by an ultrasonic generator to disrupt and disperse the particles coagulated on the surface of the air bubbles has been employed. In addition, application to poorly water-soluble pharmaceutical compounds is not suggested at all.

DOCUMENT LIST

Patent Document patent document 1: JP-A-2011-194366

Non-Patent Documents non-patent document 1: International Journal of Nanomedicine 2008:3(3) 295-309
non-patent document 2: European Journal of Pharmaceutical Sciences 2003:18 113-120

SUMMARY OF THE INVENTION

Problems to be Solved by the Invention

An object of the present invention is to provide fine solid particles of a pharmaceutical compound having a uniform particle size, which permit dispersibility, absorbability and formulation, by using a poor solvent precipitation method (e.g., poor solvent crystallization method) and without requiring a microparticulation treatment after precipitation, and a production method thereof.

Means of Solving the Problems

The present inventors have conducted intensive studies in an attempt to achieve the above-mentioned object and found that solid particles, which are microparticulate and show more uniform particle size distribution as compared to that by the use of regular water, can be obtained by using, in a poor solvent precipitation method (e.g., poor solvent crystallization method) of a poorly water-soluble pharmaceutical compound, water containing nanobubbles (hereinafter to be referred to as nanobubble water) or an aqueous solution containing nanobubbles (hereinafter to be referred to as an aqueous nanobubble solution) as a poor solvent. They have also found that solid particles precipitated by using nanobubble water or an aqueous nanobubble solution are superior in the dispersibility in a solvent than those precipitated by using regular water.

Based on these findings, the present inventors have conducted further studies and completed the present invention.

Accordingly, the present invention provides the following.
[1] A method of producing solid particles of a poorly water-soluble pharmaceutical compound, comprising mixing a solution of a poorly water-soluble pharmaceutical compound in a good solvent and nanobubble water or an aqueous nanobubble solution to precipitate solid particles of the poorly water-soluble pharmaceutical compound.

[2] The method of the above-mentioned [1], wherein the nanobubble water or aqueous nanobubble solution comprises a bubble having an average diameter of 500 nm or less.

[3] The method of the above-mentioned [1], wherein the poorly water-soluble pharmaceutical compound shows solubility of less than 15000 ppm in water at 25° C.

[4] Solid particles of a poorly water-soluble pharmaceutical compound obtained by the method of any of the above-mentioned [1]-[3].

[5] A pharmaceutical composition comprising the solid particles of the above-mentioned [4].

Effect of the Invention

In a poor solvent precipitation method (e.g., poor solvent crystallization method), solid particles of a poorly water-soluble pharmaceutical compound, which are microparticulate and have uniform particle size distribution, can be obtained by using nanobubble water or an aqueous nanobubble solution as a poor solvent. Therefore, the cost for a microparticulation treatment after precipitation and a decrease in the yield can be avoided. Since nanobubbles prepared by pressurized dissolution are stably present in water, microparticle crystals can be produced without the need for generating nanobubbles during production of fine particles, but by using nanobubble water/aqueous solution prepared in advance by pressurized dissolution, whereby production of fine particles becomes more convenient. When a fine particle preparation of a poorly water-soluble pharmaceutical compound is formulated as a sterile preparation, a sterilization treatment is essential. When microparticulation is performed using a bead mill and the like, a new aseptic drug substance preparation steps (filtration sterilization step, freeze-dry step, milling step etc.) become necessary, which increases the production step. In the poor solvent precipitation method of the present invention, the sterilization step is solely a filtration sterilization step, and the cost and the number of steps relating to the sterilization treatment can be reduced. When a poorly water-soluble pharmaceutical compound is formulated as an aqueous liquid medicine, the dispersibility in a solvent is improved, and it can be formulated even without adding a suspending agent to the solvent. Moreover, the absorbability and sustainability of the drug in the body are improved. When prepared as an injection, microparticulation enables use of a thinner injection needle, whereby a burden on the patients can be reduced.

DETAILED DESCRIPTION OF THE INVENTION

Figure 1:
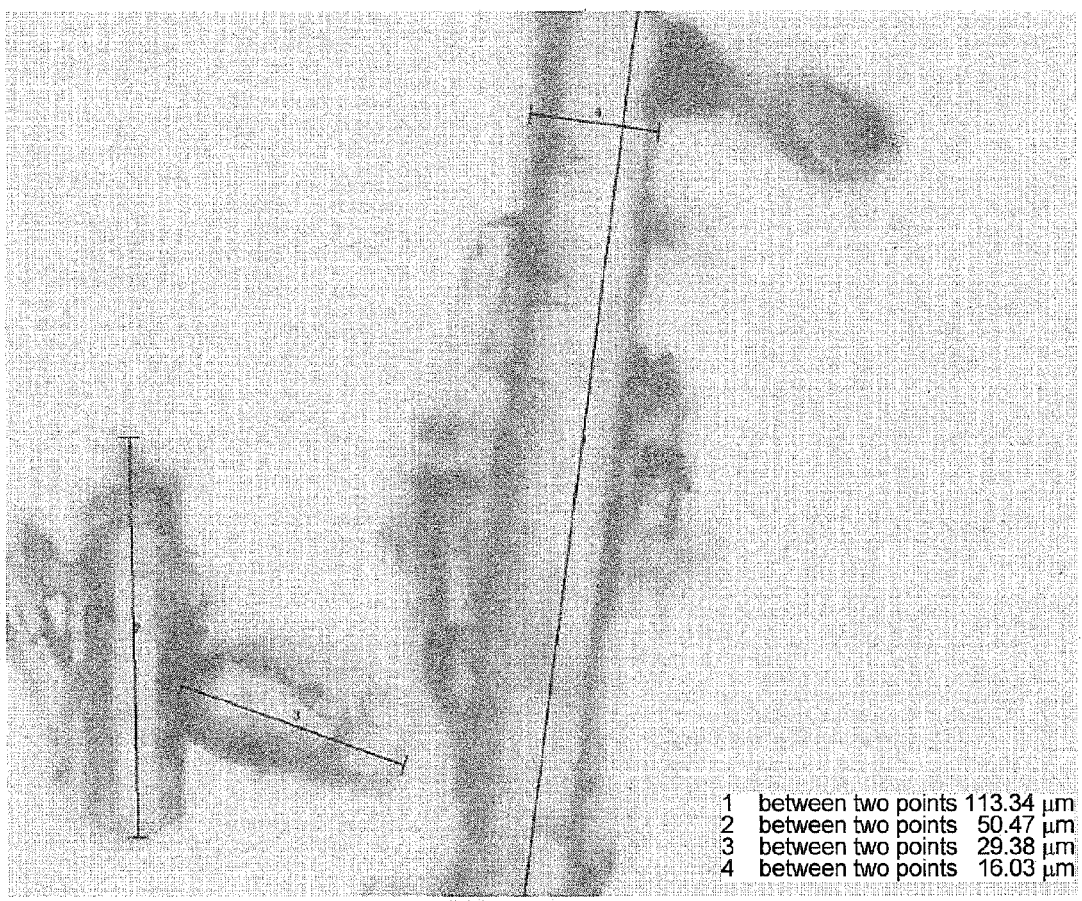
FIG. 1 is a microscopic photograph of the crystals of resatorvid precipitated by poor solvent crystallization using regular water for injection as a poor solvent.

The production method of solid particles of a poorly water-soluble pharmaceutical compound of the present invention is characterized by mixing a solution of a poorly water-soluble pharmaceutical compound in a good solvent and nanobubble water or an aqueous nanobubble solution to allow for precipitation of the solid particles of the poorly water-soluble pharmaceutical compound.

In the present specification, "solid particles" mean crystal or atypical crystal, preferably crystal. The crystal may have a single crystal form or may be a mixture of crystal forms. The crystal may be a pharmaceutically acceptable cocrystal or a cocrystal salt. Here, the cocrystal or cocrystal salt means a crystalline substance constituted of two or more unique solids at room temperature, each having different physical properties (e.g., structure, melting point, heat of fusion, hygroscopicity, solubility, stability etc.).

In the present specification, the "precipitation method" means a precipitation method of solid particles utilizing a solid particulation phenomenon in a non-equilibrium state, wherein supersaturation is the driving power, and is preferably a crystallization method.

In the present specification, the "crystallization method" means a precipitation method of a crystal utilizing a crystallization phenomenon in a non-equilibrium state, wherein supersaturation is the driving power.

In the present specification, the "poor solvent precipitation method" means a method of precipitating solid particles by dissolving, in a good solvent, a compound insoluble in water and the like, mixing the compound solution with another solvent (water etc.) to place the solution in a supersaturation state, and is preferably a poor solvent crystallization method.

In the present specification, the "poor solvent crystallization method" means a method of precipitating a crystal by dissolving, in a good solvent, a compound insoluble in water and the like, mixing the compound solution with another solvent (water etc.) to place the solution in a supersaturation state.

In the present specification, being "poorly water-soluble" means solubility of less than 15000 ppm, preferably less than 150 ppm, in water at 25° C., or solubility of less than 15 mg/mL, preferably less than 0.05 mg/mL, in water at 25° C. Therefore, being "poorly water-soluble" in the present specification also includes water insolubility. The solubility can be measured by a conventional method (see, for example, the Japanese Pharmacopoeia 16th edition, pages 37-40).

Examples of the poorly water-soluble pharmaceutical compound include the following compounds and salts thereof
(1) Drugs for Lowering Fever, Pain Relief, Anti-Inflammation salicylic acid, sulpyrine, flufenamic acid, Diclofenac, indomethacin, atropine, scopolamine, morphine, pethidine, levorphanol, ketoprofen, naproxen, ibuprofen, oxymorphone, aspirin, aminopyrine, phenacetin, acetaminophen, phenylbutazone, ketophenylbutazone, mefenamic acid, bucolome, benzydamine, mepirizole, tiaramide, tinoridine, kylocaine, pentazocine, dexamethasone, hydrocortisone, prednisolone, azulene, isopropylantipyrine, sasapyrine, clofezone, etodola or a salt thereof and the like;

(2) Tranquilizers diazepam, lorazepam, oxazepam, oxazolam, clotiazepam, medazepam, temazepam, fludiazepam, meprobamate, nitrazepam, chlordiazepoxide and the like;

(3) Antipsychotic Agents chlorpromazine, prochlorperazine, trifluoperazine, sulpiride, clocapramine hydrochloride, zotepine, haloperidol and the like;

(4) Antibacterial Agents griseofulvin, lankacidin-group [Journal of Antibiotics (J. Antibiotics), 38, 877-885(1985)], azole compound [2-[(1R, 2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3-(2H,4H)-1,2,4-triazolone, fluconazole, itraconazole and the like], nalidixic acid, piromidic acid, pipemidic acid trihydrate, enoxacin, cinoxacin, ofloxacin, norfloxacin, ciploxacin hydrochloride, sulfamethoxazole.trimethoprim and the like;

(5) Antibiotics
gentamicin, dibekacin, kanendomycin, lividomycin, tobramycin, amikacin, Dibekacin, fradiomycin, sisomicin, tetracycline, oxytetracycline, rolitetracycline, doxycycline, ampicillin, piperacillin, ticarcillin, cephalothin, cephaloridine, cefotiam, cefotiam hexetil, cefsulodin, cefmenoxime, cefmetazole, cefazolin, cefotaxime, cefoperazone, ceftizoxime, moxalactam, thienamycin, sulfazecin, aztreonam, amoxicillin, cefalexin, erythromycin, bacampicillin, minocycline, chloramphenicol or a salt thereof and the like;

(6) Antitumor Drugs
6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, HER2 inhibitors (heterocyclic compounds described in WO 98/03505A and WO 01/77107A and the like, etc.), taxol, doxorubicin hydrochloride, etoposide, mitoxantrone, mesna, dimesna, aminoglutethimide, tamoxifen, acro line, cisplatin, carboplatin, cyclophosphamide, lomustine (CCNU), carmustine (BCNU) and the like;

(7) Antihypolipidemic Drugs
clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], clinofibrate, colestyramine, soysterol, tocopherol nicotinate, nicomol, niceritrol, probucol, elastase and the like;

(8) Antitussive and Expectorant Drugs
ephedrine, methylephedrine, noscapine, codeine, dihydrocodeine, alloclamide, chlophedianol, picoperidamine, cloperastine, protokylol, isoproterenol, salbutamol, terputaline, terbutaline, bromhexine, carbocystine, ethylcystine, methylcystine or a salt thereof and the like;

(9) Muscle Relaxants
pridinol, tubocurarine, pancuronium, chlorphenesin carbamate, tolperisone hydrochloride, eperisone hydrochloride, tizanidine hydrochloride, mephenesin, chlorzoxazone, phenprobamate, methocarbamol, chlormezanone, pridinol mesylate, afloqualone, baclofen, sodium dantrolene and the like;

(10) Antiepileptic Drugs
phenytoin, ethosuximide, acetazolamide, chlordiazepoxide, phenobarbital, carbamazepine, primidone and the like;

(11) Antiulcer Agents
lansoprazole, metoclopramide, famotidine, omeprazole, sulpiride, trepibutone, cetraxate hydrochloride, gefarnate, irsogladine maleate, cimetidine, ranitidine hydrochloride, nizatidine, roxatidine acetate hydrochloride and the like;

(12) Antidepressants
imipramine, clomipramine, noxiptiline, phenelzine and the like;

(13) Antiallergic Drugs
diphenhydramine, chlorpheniramine, tripelennamine, metodilamine, clemizole, diphenylpyraline, methoxyphenamine, clemastine fumarate, cyproheptadine hydrochloride, mequitazine, alimemazine tartrate and the like;

(14) Cardiac Stimulants
trans-π-oxocamphor, terephyllol, aminophylline, etilefrine and the like;

(15) Therapeutic Drugs for Arrhythmia
propranolol, alprenolol, bufetolol, oxprenolol, procaineamide hydrochloride, disopyramide, ajmaline, quinidine sulfate, aprindine hydrochloride, propafenone hydrochloride, mexiletine hydrochloride and the like;

(16) Vasodilators
oxyfedrine, diltiazem, tolazoline, hexobendine, bamethan, nifedipine, isosorbide dinitrate, diltiazem hydrochloride, trapidil, dipyridamole, dilazep hydrochloride, verapamil, nicardipine hydrochloride, ifenprodil tartrate, cinepazide maleate, cyclandelate, cinnarizinee, pentoxifylline and the like;

(17) Hypotensive Diuretics
hexamethonium bromide, pentolinium, mecamylamine, ecarazine, clonidine, diltiazem, nifedipine, furosemide, trichloromethyazide, methyclothiazide, hydrochlorothiazide, hydroflumethiazide, ethiazide, cyclopenthiazide, chlorothiazide, ethacrynic acid and the like;

(18) Therapeutic Drugs for Diabetes
glymidine, glipizide, phenformin, buformin, metformin, glibenclamide, tolbutamide and the like;

(19) Antituberculosis Drugs
isoniazid, ethambutol, para-aminosalicyl acid and the like;

(20) Narcotic Antagonists
levallorphan, nalorphine, naloxone or a salt thereof and the like;

(21) Hormone Drugs
steroid hormone, for example, dexamethasone, hexestrol, methimazole, betamethasone, triamcinolone, triamcinolone acetonide, fluocinolone acetonide, prednisolone, hydrocortisone, estriol and the like;

(22) Prophylactic or Therapeutic Drugs for Disorder of Bone/Cartilage
nonpeptidic bone formation promoting action substances such as prostaglandin A1 derivative, vitamin D derivative, vitamin $K_2$ derivative, eicosapentaenoic acid derivative, benzylphosphonic acid, bisphosphonic acid derivative, sex hormone derivative, phenolsulfophthalein derivative, benzothiopyran or benzothiepin derivative, thienoindazole derivative, menatetrenone derivative, helioxanthin derivative and the like, peptidic bone formation promoting substance and the like;

(23) Therapeutic Drugs for Articular Disease
anti-inflammatory steroids such as p38MAP kinase inhibitors (thiazole compounds described in WO 00/64894 and the like, etc.), matrix metalloprotease inhibitor (MMPI), prednisolone, hydrocortisone, methylprednisolone, dexabetamethasone, betamethasone and the like, non-steroidal antiphlogistics such as indomethacin, diclofenac, loxoprofen, ibuprofen, piroxicam, sulindac and the like, and the like;

(24) Therapeutic Drugs for Frequent Urination
flavoxate hydrochloride, oxybutynin hydrochloride, terodiline hydrochloride and the like;

(25) Anti-Androgen Drugs
oxendolone, allylestrenol, chlormadinone acetate, gestonorone caproate, osapuron acetate, flutamide, bicartamide and the like;

(26) Liposoluble Vitamins
vitamin K (vitamin $K_1$, $K_2$, $K_3$ and $K_4$), folic acid (vitamin M) and the like;

(27) Vitamin Derivatives
various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like;

(28) Drugs for Sepsis.Septic Shock
Toll-like receptor (TLR) signal inhibitors (WO 99/46242, WO 01/10826), for example, ethyl (6R)-6-[(2-chloro-4-fluoroanilino)sulfonyl]-1-cyclohexene-1-carboxylate(d-ethyl 6-[N-(2-chloro-4-fluorophenyl)sulfamoyl]-1-cyclohexene-1-carboxylate) (resatorvid), ethyl (3S)-3-[N-(2-chloro-4-fluorophenyl)sulfamoyl]-3,6-dihydro-2H-pyran-4-carboxylate and the like;

(29) Others hydroxycam, diacerein, megestrol acetate, nicergoline, prostaglandins and the like;

Furthermore, known pharmaceutical compounds such as therapeutic drugs for ischemic diseases, therapeutic drugs for immune diseases, therapeutic drugs for Alzheimer's disease, therapeutic drugs for osteoporosis, therapeutic drugs for angiogenesis, therapeutic drugs for retinopathy, therapeutic drugs for retina intravenous obstruction, senile disciform macular degeneration, therapeutic drugs for cerebrovascular contraction, therapeutic drugs for cerebral thrombus, therapeutic drugs for cerebral infarction, therapeutic drugs for brain obstruction, therapeutic drugs for intracerebral bleeding, therapeutic drugs for subarachnoid hemorrhage, therapeutic drugs for hypertensive encephalopathia, therapeutic drugs for transient cerebral ischemic attack, therapeutic drugs for multiple infarction, therapeutic drugs for arteriosclerosis, therapeutic drugs for Huntington's disease, therapeutic drugs for brain tissue disorder, therapeutic drugs for optic nerve, therapeutic drugs for glaucoma, therapeutic drugs for ocular hypertension diseases, therapeutic drugs for retina detachment, therapeutic drugs for arthritis, anti-rheumatic drugs, antiasthmatic drugs, therapeutic drugs for atopic dermatitis, therapeutic drugs for allergic rhinitis, therapeutic drugs for bipolar disorders, therapeutic drugs for obesity, therapeutic drugs for hormone diseases and the like can also be used in the present invention as long as the definition of the above-mentioned "poorly water-soluble" is fulfilled.

Examples of the salt of the above-mentioned compound include pharmacologically acceptable salts, for example, salt with inorganic base, salt with organic base, salt with inorganic acid, salt with organic acid, salt with basic or acidic amino acid and the like.

Preferable examples of the salt with inorganic base include salts with alkali metals such as sodium, potassium and the like, alkaline earth metals such as calcium, magnesium and the like, and salts with aluminum, ammonium and the like.

Preferable examples of the salt with organic base include salts with trimethylamine, triethylamine, pyridine, picoline, ethanolamine, diethanolamine, triethanolamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

The poorly water-soluble pharmaceutical compound in the present specification may be a peptide having a physiological activity.

The poorly water-soluble pharmaceutical compound in the present specification preferably has a molecular weight of 200-1000.

While the "easily solvent" used in the present invention is not particularly limited as long as a given poorly water-soluble pharmaceutical compound shows a high solubility therein. For example, a solvent in which a poorly water-soluble pharmaceutical compound shows a solubility of not less than 150000 ppm or not less than 150 mg/mL, at 25° C. can be used. Specifically, while it varies depending on the kind of the poorly water-soluble pharmaceutical compound, for example, organic solvents (e.g., methanol, ethanol, 1-propanol, 2-propanol, acetone, 2-butanone, acetonitrile, ethyl acetate, n-propyl acetate, tetrahydrofuran, toluene, hexane, heptane, phosphoric acid, acetic acid, benzyl alcohol and the like, which may be a combination of one or more kinds), a mixed solvent of one or more kinds of organic solvents and water and the like can be mentioned. In poor solvent precipitation method (preferably poor solvent crystallization method) used industrially, a mixed solvent after recovery of solid particles (preferably crystals) precipitated by solid-liquid separation is further subjected to liquid-liquid separation and a process of reutilizing the organic solvent is adopted. When this process is performed by distillation and the like, it is disadvantageous in terms of the energy cost. Therefore, an organic solvent that mutually dissolves with water at a low temperature but shows two phase separation at a high temperature without mutual dissolution, for example, diisopropylamine (DiPA), N,N-dimethylisopropylamine (DMiPA) and the like can also be used as good solvents.

The concentration of a poorly water-soluble pharmaceutical compound in a good solvent, which is to be subjected to a precipitation (preferably crystallization) step of solid particles, is not particularly limited as long as an apparent concentration of a mixture of a good solvent and nanobubble water or aqueous nanobubble solution as a poor solvent is within the supersaturation region, when a solubility curve of the poorly water-soluble pharmaceutical compound at the temperature of precipitation (preferably crystallization) of solid particles is expressed on a three-component phase diagram of poorly water-soluble pharmaceutical compound-good solvent-water.

Next, a good solvent containing the poorly water-soluble pharmaceutical compound dissolved therein and nanobubble water or an aqueous nanobubble solution are mixed to precipitate (preferably crystallize) solid particles.

In the present specification, the "nanobubble water" means water wherein gas particles having a diameter of 1 μm or below (nanobubbles) are stably present. The diameter of nanobubbles (nanobubble diameter) is preferably not more than 800 nm, more preferably not more than 500 nm. While the lower limit of the nanobubble diameter is not particularly limited, it is, for example, not less than 1 nm, preferably not less than 5 nm, more preferably not less than 10 nm. While the average diameter of the nanobubbles can be appropriately determined within the range of not more than 500 nm, preferably 1-500 nm, it is appropriately determined within the range of preferably 5-300 nm, more preferably 10-150 nm. In the present specification, the average diameter means a particle size (mode diameter) corresponding to the mode value of the distribution.

The size of the nanobubbles is desirably uniform, and the d90/d10 ratio is preferably not more than 5, more preferably not more than 4.5, wherein nanobubble diameters corresponding to cumulative 10% and cumulative 90% from the small diameter side of the nanobubble diameter distribution are d10 and d90, respectively.

The nanobubble diameter and the distribution thereof can be measured by a method utilizing scattering of a laser beam based on the Brownian motion (e.g., NanoSight Ltd., LM20 and the like), a method based on impedance change (e.g., Beckman Coulter Inc., Multisizer 4 and the like), a method based on laser diffraction scattering method (e.g., Shimadzu Corporation, SALD-7100H and the like), a method utilizing Mie scattering (e.g., Nippon Denshoku Industries Co., Ltd., NP-500T and the like) and the like. As the nanobubble diameter of the nanobubble water or aqueous nanobubble solution to be used in the present invention and the distribution thereof, those measured by a tracking method utilizing laser beam scattering by using LM20, NanoSight Ltd., or those measured according thereto are used.

The density of nanobubbles contained in nanobubble water is not particularly limited as long as, in poor solvent crystallization, solid particles of a poorly water-soluble pharmaceutical compound, which are more microparticulate and have uniform particle size distribution, can be significantly precipitated, as compared to when regular water free of nanobubbles is used as a poor solvent. For example, it is desirably not less than $10^5$ nanobubbles/mL, preferably not less than $10^6$ nanobubbles/mL, more preferably not less than $10^7$ nanobubbles/mL. The upper limit of the nanobubble density is not particularly limited, and may be of the level producible by a conventional nanobubble generator (e.g., not more than $10^9$ nanobubbles/mL). The nanobubble density can also be measured by the above-mentioned apparatus for measuring the nanobubble diameter.

That nanobubbles are "stably present" means that, in a poor solvent precipitation method (preferably, poor solvent crystallization method), solid particles of a poorly water-soluble pharmaceutical compound are present in water in the state where the above-mentioned nanobubble density conditions are maintained for a time sufficient for the solid particles to be precipitated. In nanobubble water or aqueous nanobubble solution produced by a general nanobubble generator, the half-life of nanobubbles is several days to several months.

Examples of the gas constituting the nanobubbles include, but are not limited to, oxygen, ozone, nitrogen, carbon dioxide, helium etc., a mixture of one or more gases selected from oxygen, ozone, nitrogen, carbon dioxide, helium and the like, and the like. Examples of the mixture include, but are not limited to, gases in the air (e.g., air) and the like. The inside of nanobubbles may be vacuum.

In the present specification, "vacuum" means the state of a space filled with a gas with a lower pressure than normal atmosphere.

On the other hand, "water" containing nanobubbles is not particularly limited and, for example, tap water, deionized water, distilled water, sterile distilled water, purified water for injection, ultrapure water and the like can be used. When the object poorly water-soluble pharmaceutical compound is a pharmaceutical compound, it is desirable to use pharmaceutically acceptable "water".

In the present specification, "aqueous solution" refers to an aqueous solution further containing, in water, any additive usable by adding to a poor solvent in a general poor solvent precipitation method (preferably, poor solvent crystallization method). Examples of such additive include excipient, lubricant, binder, disintegrant, solubilizing agent, suspending agent, isotonicity agent, buffering agent, soothing agent, preservative, antioxidant, colorant, sweetening agent, pH adjuster, surfactant, stabilizer, acidulant, flavor, fluidizer and the like. Preferable examples thereof are those similar to the following pharmacologically acceptable carriers.

Two or more kinds of the above-mentioned additives can be mixed and used at an appropriate ratio. As the additive, preferred are one or more additives selected from surfactant (preferably, polysorbate 80 and the like), suspending agent, stabilizer, dispersing agent, isotonicity agent and the like. As long as the production and/or stability of nanobubbles and/is not influenced, these additives can be dissolved in water in advance and directly prepared as an aqueous nanobubble solution. It is also possible to produce nanobubbles in water free of additive to give nanobubble water, and dissolve additives therein when in use to give an aqueous nanobubble solution.

The production methods of nanobubble water are largely divided into a method comprising simultaneously generating microbubbles (gas particles having a diameter of about 1-60 μm) and nanobubbles in water, and floatation separating the microbubbles to leave only nanobubbles, and a method comprising directly generating nanobubbles, and the former is mainly employed at present. The former method includes a high-speed swirling flowing method wherein a gas is disrupted by high-speed whirling to generate many microbubbles, and the microbubbles are floatation separated to leave nanobubbles in water, a pressurized dissolution method wherein a gas is pressurized to be dissolved in water at supersaturation, the solution is rapidly depressurized to allow generation of microbubbles and nanobubbles, and the microbubbles are floatation separated to leave nanobubbles in water, and the like.

Examples of the gas constituting the microbubbles include, but are not limited to, oxygen, ozone, nitrogen, carbon dioxide, helium etc., a mixture of one or more gases selected from oxygen, ozone, nitrogen, carbon dioxide, helium and the like, and the like. Examples of the mixture include, but are not limited to, gases in the air (e.g., air) and the like. The inside of microbubbles may be vacuum.

The production method of nanobubble water is preferably a pressurized dissolution method. For example, a gas is forcively dissolved in a pressurized vessel pressurized by a pressure pump to about 0.2-0.5 MPa, which is flushed into water through a nozzle. As a result, the gas depressurized to reach supersaturation is released as microbubbles or nanobubbles in the drain to form a mixture of cloudy microbubble water and nanobubble water. Thereafter, aeration is discontinued and the mixture is stood to allow for natural floatation defection of microbubbles. Consequently, clear nanobubble water containing only nanobubbles is formed. Accordingly, the pressurized dissolution method wherein bubbles are generated secondarily via a 2-step process of precipitation by pressurized dissolution—depressurization is different from other methods wherein bubbles are directly formed from a gas sucked in the working fluid.

Examples of a nanobubble generator include pressurized dissolution method nanoGALF™ manufactured by IDEC, OM4-MD5-045 manufactured by Aura Tec, a microbubble generator and the like manufactured by NIKUNI Co., Ltd., high-speed swirling flow type YJ manufactured by Bi-Clean, a microbubble generator manufactured by Aqua-Air, a microblade manufactured by Royal Electric Co., Ltd. and the like. A preferable nanobubble generator is pressurized dissolution method nanoGALF™ manufactured by IDEC.

Solid particles can be precipitated at, for example, 10-60° C., preferably 15-40° C.

Crystallization can be performed at, for example, 10-60° C., preferably 15-40° C.

To obtain crystals superior in the filtration property and separation property according to the kind of the object compound, and suppress coagulation and scaling of crystals, it is also possible to perform a step for forming crystals and aging the formed crystals before addition of nanobubble water or aqueous nanobubble solution.

The method for forming crystals is not particularly limited and, for example, (i) a method of adding water, (ii) a method of adding seed crystal, (iii) a method of lowering the temperature of solution and the like can be mentioned. These methods can also be combined freely. For example, when the aforementioned (i) and (ii) are combined, the seed crystal can be added simultaneously with water or thereafter.

The amount of water to be added in (i) may be an amount that induces formation of the crystal of a poorly water-soluble pharmaceutical compound. While the temperature of water to be added in (i) is not particularly limited, it is preferably similar to the crystallization temperature.

The amount of the seed crystal to be added in (ii) can be appropriately determined, and is generally preferably about 0.01%-3% relative to the object compound present in the solution. Aging to be performed after crystal formation is preferably performed with stirring. While the time of aging is not particularly limited it may be, for example, about 10 min-24 hr, preferably about 30 min-2 hr.

In the case of an amorphous form, it is also possible to perform a step for forming crystals and aging the formed crystals before addition of nanobubble water or aqueous nanobubble solution, according to the above-mentioned method.

A poorly water-soluble pharmaceutical compound solution and nanobubble water or aqueous nanobubble solution can be mixed by the addition of the latter to the former, or the former to the latter. In any case, to prevent easy coagulation of solid particles (preferably crystal), development of scaling and the like, the poorly water-soluble pharmaceutical compound solution, or nanobubble water or aqueous nanobubble solution is preferably stirred as appropriate during addition. The stirring conditions can be appropriately set to those free of such problems by those of ordinary skill in the art with ease.

The stirring rate for crystallization is, for example, within the range of 10-50000 rpm.

The mixing ratio of the poorly water-soluble pharmaceutical compound solution and the nanobubble water or aqueous nanobubble solution also varies depending on the conditions such as the concentration of the poorly water-soluble pharmaceutical compound, temperature of precipitation (preferably, crystallization) of the solid particles and the like, and is not particularly limited. It is generally about 0.1-400, preferably 0.5-200, in volume ratio, relative to the good solvent at the time of the start of the precipitation (preferably, crystallization) of solid particles. The mixing speed of the compound solution and the nanobubble water or aqueous nanobubble solution (addition speed of compound solution, nanobubble water, or aqueous nanobubble solution) is not particularly limited, and they can be gradually added for generally about 1 min-5 hr. Preferable mixing ratio, mixing speed and the like can be appropriately set by those of ordinary skill in the art with ease according to various conditions.

The precipitated solid particles (preferably crystal) of a poorly water-soluble pharmaceutical compound can be recovered by solid-liquid separation according to a conventional method. Where necessary, they can be washed with water or a mixture of water and alcohol, and the like, and dried by vacuum drying and the like.

The present invention is characterized in that, in a poor solvent precipitation method (preferably, poor solvent crystallization method), solid particles (preferably crystal) of the object compound, which are more microparticulate and have uniform particle size distribution, can be obtained by using a solvent containing nanobubbles as a poor solvent, as compared to when the same solvent free of nanobubbles is used. In the present specification, since the description mostly concerns the case when the object compound is a pharmaceutical compound, a production method of a crystal of a poorly water-soluble pharmaceutical compound, which comprises mixing a solution of poorly water-soluble pharmaceutical compound in a good solvent and nanobubble water or aqueous nanobubble solution, is explained in detail. Similarly, however, microparticulate and uniformly solid particles (preferably crystal) of an easily water-soluble compound can also be produced by mixing a solution of the compound in a good solvent (e.g., water) and a poor solvent (e.g., organic solvent miscible with water, which does not easily dissolve the object compound) containing nanobubbles. As the apparatus, a mixed crystal precipitation apparatus, a high-pressure crystallization apparatus (PureNano etc.) and the like can be mentioned.

Also, in the present invention, the particles may be ground when desired by a generally-used milling machine in addition to the above-mentioned poor solvent precipitation method (preferably, poor solvent crystallization method). Examples of the milling machine include mortar, mecchanomill, jet mill, ball mill, Wet-Milling apparatus and the like.

The apparatus to be used also includes homogenizer, high-pressure homogenizer (Microfluidizer etc.), Starburst and the like.

The solid particles (preferably crystal) of a poorly water-soluble pharmaceutical compound obtained as mentioned above are novel since they are microparticulate and have uniform particle size distribution as compared to solid particles (preferably crystal) that precipitated using normal water as a poor solvent. To be specific, each of the solid particles (preferably crystal) of a poorly water-soluble pharmaceutical compound of the present invention, when without a microparticulation treatment after precipitation, has a maximum length (length of the longest part) of not more than 1500 μm on average, and not less than 90% of the total solid particles (preferably crystal) has a maximum length of not more than 1500 μm.

The solid particles (preferably crystal) of a poorly water-soluble pharmaceutical compound obtained as mentioned above are novel since they have stable dispersibility as compared to solid particles (preferably crystal) that precipitated using normal water as a poor solvent. To be specific, the solid particles (preferably crystal) of a poorly water-soluble pharmaceutical compound of the present invention shows an absolute value of zeta potential, which is an index of the stability in a dispersion state, of not less than 20 mV. Also, the solid particles (preferably crystal) of a poorly water-soluble pharmaceutical compound of the present invention has a settling velocity, which is an index of the solubility, of not more than 50 cm/min.

In the present specification, the "zeta potential" of the solid particles of a poorly water-soluble pharmaceutical compound refers to a potential difference between the surface of a liquid layer (slipping plane) that moves together with solid particles of the compound dispersed in a dispersing medium, and an electrically neutral region sufficiently distant from the solid particles, at the pH of a dispersing medium used for formulating the poorly water-soluble pharmaceutical compound as a suspension.

When a given voltage E is applied to a solution, a relationship expressed by $\zeta = \eta v/\in E$ ($\eta$: viscosity of dispersing medium, $\in$: dielectric constant of dispersing medium) stands between zeta potential $\zeta$ and relative velocity v of the movement on slipping plane. Therefore, zeta potential can be measured by measuring the relative velocity v of the movement on the slipping plane. As a specific measurement method of the zeta potential, electrophoresis is mainly used. When an electric field E is applied to a quartz cell having electrodes embedded on both ends, the particles move toward the electrode having the opposite polarity. The moving velocity (migration velocity) is in proportion to the electric charge state of the particles. The moving velocity is directly measured using a stopwatch under a microscope, or measured by irradiating a laser beam and projecting an image of the dispersion particles on a diffraction grating surface via an object lens, and a moving velocity (electrophoretic mobility) v/E per unit electric field is determined and inserted into the above formula to convert same to a zeta potential. Using a method of analyzing the frequency shifted by a Doppler effect (Doppler frequency), information relating to the distribution of zeta potential can also be obtained. As a zeta potential measurement device using a laser-Doppler method, for example, Zetasizer Nano manufactured by Malvern can be used.

In the present specification, the "settling velocity" is the speed of settling of the particles in a container.

As for the settling velocity, the thickness of particle settling per time is measured using a measuring cylinder, and calculated by a calculation formula (see 39th Geotechnical workshop proceedings pages 2247-2248 (public interest incorporated association, Japanese Geotechnical Society, published June 2004)). To be specific, solid particles of a poorly water-soluble pharmaceutical compound are suspended in a dispersing medium, the suspension is placed in a measuring cylinder, which is capped with a film and shaken up and down for sufficient infiltration. The measuring cylinder is stood, the scale of the measuring cylinder at a level corresponding to the solid-liquid interface is read at every given time, and a settling curve showing the relationship between the settling amount (distance from liquid level to solid-liquid interface) and the time is formed from the results thereof. The slope of the initial tangent line against the settling curve is determined as a settling velocity.

As mentioned above, since the poor solvent precipitation method (preferably poor solvent crystallization method) of the present invention enables advanced control (e.g., microparticulation, homogenization) of the quality of solid particles (preferably crystal) of the object compound, when precipitated solid particles (preferably crystal) of a poorly water-soluble pharmaceutical compound of the present invention are formulated as an aqueous liquid medicine (suspension), they are easily suspended in an aqueous solvent, and can be uniformly dispersed with ease even without adding a suspending agent and the like to the solvent. Particularly, when they are prepared as an injection, a narrow injection needle can be used by microparticulation, thus reducing the burden on patients due to injection. Furthermore, it is also possible to increase absorbability of a poorly water-soluble pharmaceutical compound from the administration site in animals.

In addition to the above-mentioned advantages, since nanobubble water or an aqueous nanobubble solution is used, the precipitated solid particles (preferably crystal) of a poorly water-soluble pharmaceutical compound in the present invention may have different shape and/or surface charge of solid particles (preferably crystal) from those of solid particles (preferably crystal) precipitated using regular water as a poor solvent. Moreover, since free radical is generated in nanobubble water or aqueous nanobubble solution, they may have, due to an influence thereof, properties different from those of crystals precipitated using regular water or an aqueous solution thereof as a poor solvent. Also from these aspects, the precipitated solid particles (preferably crystal) of a poorly water-soluble pharmaceutical compound in the present invention are novel solid particles (preferably crystal) different from known solid particles (preferably crystal) precipitated using regular water as a poor solvent.

When the solid particles (preferably crystal) of a poorly water-soluble pharmaceutical compound of the present invention are of a pharmaceutical compound, they can be directly used as a prophylactic or therapeutic agent for the below-mentioned various diseases in mammals (e.g., human, mouse, rat, rabbit, dog, cat, bovine, horse, swine, monkey) or as a pharmaceutical composition produced by mixing with a pharmacologically acceptable carrier and the like.

As the pharmacologically acceptable carrier, various organic or inorganic carrier substances conventionally used as preparation materials can be used. They are added as excipient, lubricant, binder, disintegrant for solid preparations; solvent, solubilizing agents, suspending agent, isotonicity agent, buffering agent, soothing agent for liquid preparations and the like. Where necessary, preparation additives such as preservative, antioxidant, colorant, sweetening agent, pH adjuster, surfactant, stabilizer, acidulant, flavor, fluidizer and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthesis aluminum silicate, and magnesium alumino metasilicate.

Preferable examples of the lubricant include magnesium stearate, calcium stearate, talc, and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid, and low-substituted hydroxypropylcellulose.

Preferable examples of the solvent include water for injection, saline, Ringer's solution, alcohol, propylene glycol, polyethylene glycol, sesame oil, corn oil, olive oil, and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, and polyoxyethylene hydrogenated castor oil.

Preferable examples of the isotonicity agent include sodium chloride, glycerol, D-mannitol, D-sorbitol, and glucose.

Preferable examples of the buffering agent include buffers of salt of phosphoric acid, salt of acetic acid, salt of carbonic acid, salt of citric acid and the like.

Preferable examples of the soothing agent include benzyl alcohol.

Preferable examples of the preservative include paraoxybenzoates, chlorobutanol, benzyl alcohol, phenethyl alcohol, dehydroacetic acid, and sorbic acid.

Preferable examples of the antioxidant include salts of sulfurous acid, ascorbic acid and the like.

Preferable examples of the colorant include water-soluble food tar color (e.g., food colors such as Food Color Red Nos. 2 and 3, Food Color Yellow Nos. 4 and 5, Food Blue Nos. 1 and 2 and the like), water insoluble lake pigment (e.g., aluminum salt of the aforementioned water-soluble food tar color), natural dye (e.g., β-carotene, chlorophyll, ferric oxide red).

Preferable examples of the sweetening agent include saccharin sodium, dipotassium glycyrrhizinate, aspartame, and stevia.

Examples of the dosage form of the aforementioned pharmaceutical composition include oral preparations such as tablet (including sugar-coated tablet, film-coated tablet, sublingual tablet, orally disintegrating tablet), capsule (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion, intracerebral administration injection, injection into cerebrospinal fluid, intraocular injection), external preparation (e.g., dermal preparation, ointment), suppository (e.g., rectal suppository, vaginal suppository), pellet, nasal preparations, pulmonary preparation (inhalant), eye drop and the like.

They can be each safely administered orally or parenterally (e.g., topical administration, rectal administration, intravenous administration, subcutaneous administration, intramuscular administration, transnasal administration, vaginal administration, intracerebral administration, administration into cerebrospinal fluid, instillation administration, intraocularadministration).

These preparations may be controlled-release preparations (e.g., sustained-release microcapsule) such as immediate-release preparation, sustained-release preparation and the like.

The pharmaceutical composition can be produced by a method conventionally used in the technical field of preparations, for example, the method described in the Japanese Pharmacopoeia 16th edition, and the like.

While the content of the compound of the present invention in the pharmaceutical composition varies depending on the dosage form, dose of the compound of the present invention, and the like, it is, for example, about 0.1-100 wt %.

When an oral preparation is produced, it may be coated as necessary for masking of taste, enteric coating or sustainability.

Examples of the coating base to be used for coating include a sugar coating base, a water-soluble film coating base, an enteric film coating base, a sustained-release film coating base and the like.

As the sugar coating base, sucrose is used. Furthermore, one or more kinds selected from talc, precipitated calcium carbonate, gelatin, gum arabic, pullulan, Carnauba wax and the like may be used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinylacetal diethylaminoacetate, aminoalkylmethacrylate copolymer E [Eudragit E (trade name)], polyvinylpyrrolidone and the like; polysaccharides such as pullulan and the like; and so on.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally occurring substances such as shellac and the like.

Examples of the sustained-release film coating base include cellulose polymers such as ethylcellulose and the like; acrylic acid polymers such as aminoalkylmethacrylate copolymer RS [Eudragit RS (trade name)], ethyl acrylate-methyl methacrylate copolymer suspension [Eudragit NE (trade name)] and the like; and so on.

The above-mentioned coating bases may be used as a mixture of two or more kinds thereof at an appropriate ratio. Also, a light shielding agent such as titanium oxide, red ferric oxide and the like may also be used for coating.

Examples of the pH adjuster include salts of citric acid, phosphoric acid, carbonic acid, tartaric acid, fumaric acid, acetic acid, amino acid and the like.

Examples of the surfactant include sodium lauryl sulfate, polysorbate 80, polyoxyethylene(160)polyoxypropylene(30) glycol and the like.

Examples of the stabilizer include tocopherol, tetrasodium edetate, nicotinamide, cyclodextrins and the like.

Examples of the acidulant include ascorbic acid, citric acid, tartaric acid, malic acid and the like.

Examples of the flavor include menthol, peppermint oil, lemon oil, vanillin and the like.

Examples of the glidant include light anhydrous silicic acid, hydrated silicon dioxide and the like. The light anhydrous silicic acid may be any as long as it contains hydrated silicon dioxide ($SiO_2 \cdot nH_2O$) (n is an integer) as a main component. Concrete examples thereof include Sylysia 320 (trade name, Fuji Silysia Chemical Ltd.), AEROSIL 200 (trade name, NIPPON AEROSIL CO., LTD.) and the like.

The above-mentioned additives may be used as a mixture of two or more kinds thereof at an appropriate ratio.

The present invention is explained in more detail in the following by referring to Examples, which are not to be construed as limitative.

EXAMPLES

In the following Examples and Comparative Example, ethyl (6R)-6-[(2-chloro-4-fluoroanilino)sulfonyl]-1-cyclohexene-1-carboxylate (d-ethyl 6-[N-(2-chloro-4-fluorophenyl)sulfamoyl]-1-cyclohexene-1-carboxylate) (resatorvid) was used as a poorly water-soluble pharmaceutical compound. Resatorvid was produced by the method described in WO 99/46242.

Nanobubble water was prepared under the following conditions and by using a nanobubble generator (nanoGALF™FZ1N-02) manufactured by IDEC.

air bubble water flow about 4.0 L/min
dissolution pressure 300Kpa±5%

When nanobubble water is produced by the above-mentioned method, it is known that nanobubble water containing nanobubbles having a diameter of 100 nm as a mode diameter at a number density of not less than one billion bubbles/mL, as measured by a tracking method utilizing a laser beam scattering using LM20, NanoSight Ltd., is stably produced. The thus-obtained nanobubble water is known to not show large changes in the total particle number of nanobubbles and particle size for 3 days after production, and nanobubbles are stably present in water (see Japanese Society for Multiphase Flow conference 2011, Shigeo MAEDA et al., "The high-concentrated stable production of ID 100 nm-nano-bubbles by nanoGALF technology").

Comparative Example 1

Production of Resatorvid Crystal by Crystallization Using Water for Injection as Poor Solvent Resatorvid (10 mg) was dissolved in methanol (0.5 mL) to prepare a methanol solution of resatorvid. The solution was added dropwise to water (5 mL) for injection with stirring at 600 rpm to allow precipitation of resatorvid crystal. The crystal was recovered, and vacuum dried at 50° C. for 24 hr. The obtained crystal was observed under a microscope. The results are shown in FIG. 1.

Example 1

Production of Resatorvid Crystal by Crystallization Using Nanobubble Water as Poor Solvent In the same manner as in Comparative Example 1 except that water for injection containing nanobubbles produced under the above-mentioned conditions was used instead of water for injection, resatorvid crystal was obtained. The obtained crystal was observed under a microscope. The results are shown in FIG. 2.

Figure 2:
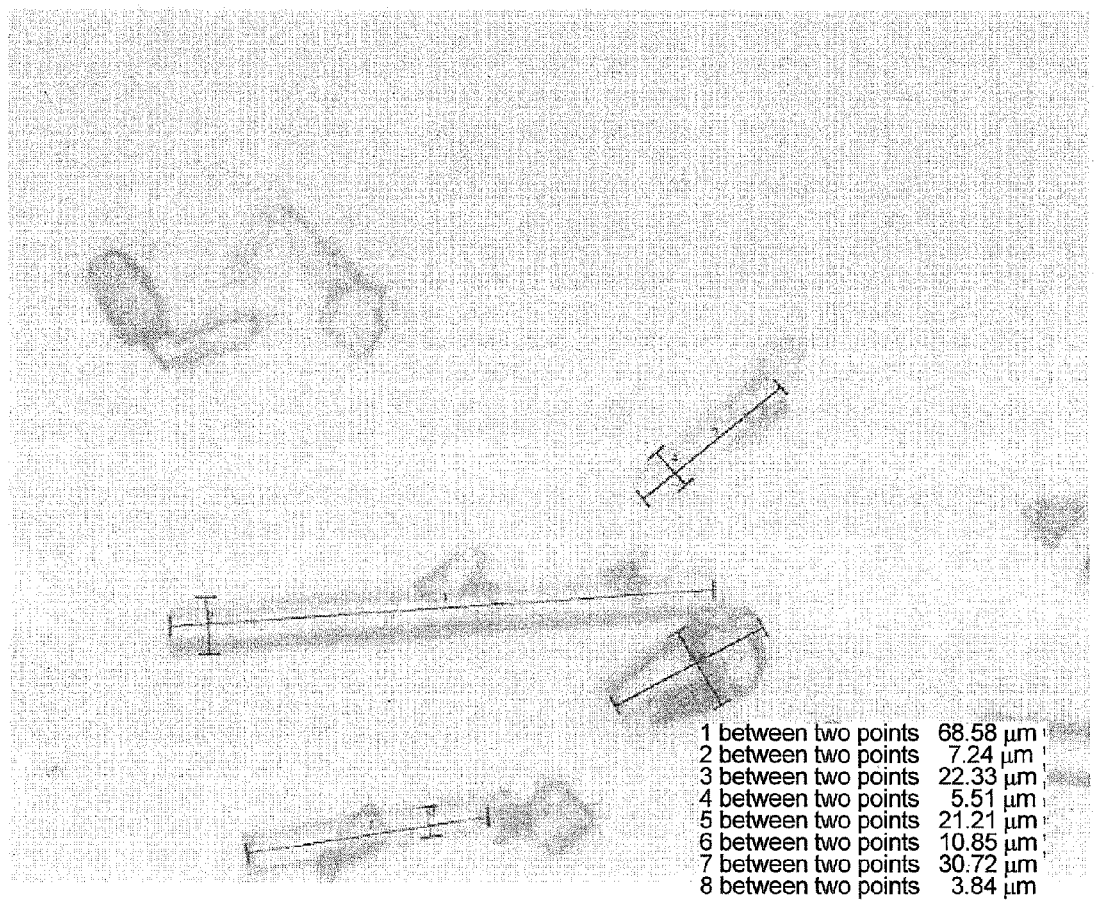
FIG. 2 is a microscopic photograph of the crystals of resatorvid precipitated by poor solvent crystallization using nanobubble water as a poor solvent.

As is clear from the comparison of FIG. 1 and FIG. 2, crystal having a smaller average maximum length of each crystal particle, as compared to when conventional water for injection was used, was obtained by using nanobubble water.

Comparative Example 2

Production of Resatorvid Crystal by Crystallization Using Aqueous Polysorbate 80 Solution as Poor Solvent Resatorvid (10 mg) was dissolved in methanol (0.5 mL) to prepare a methanol solution of resatorvid. Polysorbate 80 (2 mg) was dissolved in water for injection (10 mL) to prepare aqueous polysorbate 80 solution. The aforementioned resatorvid solution (0.5 mL) was added dropwise to water (10 mL) for injection with stirring at 600 rpm to allow precipitation of resatorvid crystal. The crystal was recovered, and vacuum dried at 50° C. for 24 hr. The obtained crystal was observed under a microscope.

Example 2

Production of Resatorvid Crystal by Crystallization Using Aqueous Polysorbate 80 Nanobubble Solution as Poor Solvent In the same manner as in Comparative Example 2 except that water for injection containing nanobubbles produced under the above-mentioned conditions was used instead of water for injection, resatorvid crystal was obtained. The obtained crystal was observed under a microscope.

Crystal having a smaller average maximum length of each crystal particle, as compared to when conventional aqueous polysorbate 80 solution was used, was obtained by using an aqueous nanobubble solution.

INDUSTRIAL APPLICABILITY

Since the poor solvent crystallization method can be operated at ambient temperature, it is advantageous in that heat denaturation of the object product can be avoided, the energy cost can also be suppressed low, and the yield of the object product can also be improved. On the other hand, since the technique for controlling the crystal quality is immature, application thereof to the production of pharmaceutical products has been limited. Since the present invention enables advanced control of the crystal quality in poor solvent crystallization, the poor solvent crystallization method can be utilized as a general purpose technique for the production of pharmaceutical products.

This application is based on a patent application No. 2012-212264 filed in Japan, the contents of which are incorporated in full herein.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A method of producing solid particles of a poorly water-soluble pharmaceutical compound, comprising mixing a solution of a poorly water-soluble pharmaceutical compound in a good solvent and nanobubble water or an aqueous nanobubble solution to precipitate solid particles of the poorly water-soluble pharmaceutical compound,
    wherein the nanobubble water or aqueous nanobubble solution comprises nanobubbles having a diameter size ratio d90/d10 of not more than 5.

2. The method according to claim 1, wherein the nanobubble water or aqueous nanobubble solution comprises nanobubbles having an average diameter of 500 nm or less.

3. The method according to claim 1, wherein the poorly water-soluble pharmaceutical compound has solubility of less than 15000 ppm in water at 25° C.

4. The method according to claim 1, wherein the method further comprises preparing the nanobubble water or an aqueous nanobubble solution by a pressurized dissolution method.

* * * * *